United States Patent
Sprague

[11] 3,988,068
[45] Oct. 26, 1976

[54] METHOD AND APPARATUS FOR DETECTING COSMETIC DEFECTS IN OPTHALMIC LENSES

[75] Inventor: Robert A. Sprague, Chelmsford, Mass.

[73] Assignee: Itek Corporation, Lexington, Mass.

[22] Filed: Dec. 19, 1974

[21] Appl. No.: 534,322

Related U.S. Application Data

[63] Continuation-in-part of Ser. No. 468,604, May 9, 1974, abandoned.

[52] U.S. Cl. ................................. 356/124; 356/239
[51] Int. Cl.² ........................................ G01N 21/32
[58] Field of Search ........... 356/124, 203, 239, 240, 356/103; 250/223 B

[56] References Cited
UNITED STATES PATENTS

| | | | |
|---|---|---|---|
| 3,030,516 | 4/1962 | Seavey | 250/223 B |
| 3,356,853 | 12/1967 | Rottmann | 356/240 |
| 3,394,263 | 7/1968 | Baker | 356/240 |
| 3,533,704 | 10/1970 | Krenmayr | 356/240 |

*Primary Examiner*—Ronald J. Stern
*Assistant Examiner*—Richard A. Rosenberger
*Attorney, Agent, or Firm*—Homer O. Blair; Robert L. Nathans; Gerald H. Glanzman

[57] ABSTRACT

Method and apparatus for detecting and analyzing cosmetic defects on the surface of ophthalmic lenses. The apparatus according to one embodiment comprises means for scanning a narrow beam of light across the lens surface under inspection together with an array of photodetectors for detecting the manner in which the scanning beam is scattered or deflected as a result of striking a defect on or beneath the lens surface. More particularly, the photodetector array is mounted around the edge of the lens in a symmetrical pattern such that by properly monitoring the outputs of the detectors and by correlating these outputs with the position of the scanning beam, information regarding the position of the defect, the type of defect, and its severity can readily be ascertained in an automatic manner.

By properly positioning the detector array around the edge of the lens, the system is able to automatically distinguish between cosmetic defects on the surface being examined and any defects which may be present on the opposite lens surface as well as between actual cosmetic defects and external surface debris such as dust or fingerprints.

By an alternative embodiment, the array of photodetectors can be replaced with an array of light sources while the laser can be replaced with an appropriate detector.

The system is particularly designed for inspecting the finished front surface of semifinished ophthalmic lenses although it has application in a variety of other fields.

25 Claims, 4 Drawing Figures

METHOD AND APPARATUS FOR DETECTING COSMETIC DEFECTS IN OPTHALMIC LENSES

This application is a continuation-in-part of copending U.S. Pat. application Ser. No. 468,604 filed May 9, 1974, now abandoned, by Robert A. Sprague and entitled METHOD AND APPARATUS FOR DETECTING COSMETIC DEFECTS IN OPHTHALMIC LENSES.

BACKGROUND OF THE INVENTION

1. Field of the Invention

The present invention relates generally to apparatus for detecting cosmetic defects in transparent components and, more particularly, to automated apparatus for detecting and analyzing scratches, bubbles, chips or other surface or subsurface defects in ophthalmic lenses.

2. Description of the Prior Art

After a surface of an ophthalmic lens has been ground and polished or otherwise provided with the desired finished curvature, it becomes necessary to inspect that surface to ensure that its quality is within acceptable tolerances. Specifically, the lens surface must be examined to ensure that scratches, chips or other cosmetic defects have not been introduced by the manufacturing operation or, at least, to ensure that any defects that are present are not serious enough to necessitate rejection of the lens. At the present time, the most common type of inspection procedure is to employ inspectors to examine the lenses one at a time as they come off the production line. Usually, the inspector merely looks through the lens at various angles with the aid of a bright light in the hope that any defects present will be found. Alternatively, he may project an image of the lens onto a suitable screen such that any defects in the lens will become visible on the screen.

There are several inadequacies with these techniques. For one thing, with human involvement, the determination of whether or not a lens is satisfactory is subjective in nature and, hence, not very precise. Different inspectors can and frequently do have different standards and as a result marginally acceptable lenses may often be unnecessarily rejected resulting in increased costs while poor quality lenses may sometimes be passed resulting in bad publicity to the manufacturer. Another problem with manual inspection is that defects in the lens surface may often be hidden by external surface debris such as fingerprints, dust and the like which can render the examination inaccurate, or, at least, necessitate that the lens be cleaned prior to inspection. Finally, in the manufacture of semifinished ophthalmic lenses wherein only one surface of the lens is completely finished (usually the front surface), discrimination must be made between defects on the finished and unfinished sides, since the tolerance standards are different. This makes the examination process even more difficult.

Automation of the lens inspection process has been suggested in recent times. However, those systems that have been publicized are not able to effectively distinguish between actual defects and mere surface dirt, or between first and second surface defects (in case of semifinished lenses) and thus are only of limited value.

SUMMARY OF A PREFERRED EMBODIMENT OF THE INVENTION

In accordance with the present invention, many of the above-described inadequacies have been significantly reduced by providing a system capable of automatically inspecting the lens for cosmetic surface and subsurface defects without necessitating human intervention or judgement. In accordance with a presently preferred embodiment, the apparatus provided includes appropriate structure for passing a narrow beam of light through the lens under inspection and examining the manner in which the beam is deflected or scattered as a result of any defects present in the lens. In a presently most preferred embodiment, examination of the light beam path is conveniently carried out by an array of photodetectors mounted in a symmetrical pattern around the edge of the lens such that in the absence of any defects on or beneath the lens surface under examination, light will not reach the detectors. When a defect is present, however, and is struck by the light beam, the detectors will receive varying amounts of illumination as a function of the position, type and orientation of the defect and will generate appropriate signals permitting automatic classification of the defect. By properly positioning and adjusting the detector array, by properly focusing the light and by including the proper light shields, light scattered as a result of surface dirt or as a result of back surface defects will, for the most part, not be seen by the detectors and, hence, will be ignored.

The light beam itself is preferably scanned across the lens surface so that the entire surface can be examined in a relatively rapid and efficient manner.

By an alternative embodiment, the light source and the detector array may be interchanged such that an array of light sources are positioned around the lens to internally illuminate the lens. When the lens is free from defects, light will be totally internally reflected within the lens and not reach an external photodetector. When, however, a defect is present in the lens, light will be scattered outwardly of the lens and be sensed by the photodetector as it examines the lens.

In general, the system provided enables rapid and accurate inspection of the surface of lenses and other transparent elements without requiring the subjective guesswork now employed. It is useful not only in detecting defects but also in obtaining quantitative data about the defects to provide good classification and to help in identifying problem areas in the lens manufacturing operation for use in improving the manufacturing operation. The system provided has also been designed so that it may be incorporated into existing production lines without necessitating excessive redesign thereof. Yet, further features of the invention will be set out in greater detail hereinafter.

DETAILED DESCRIPTION OF THE PREFERRED EMBODIMENTS

Figure 1:
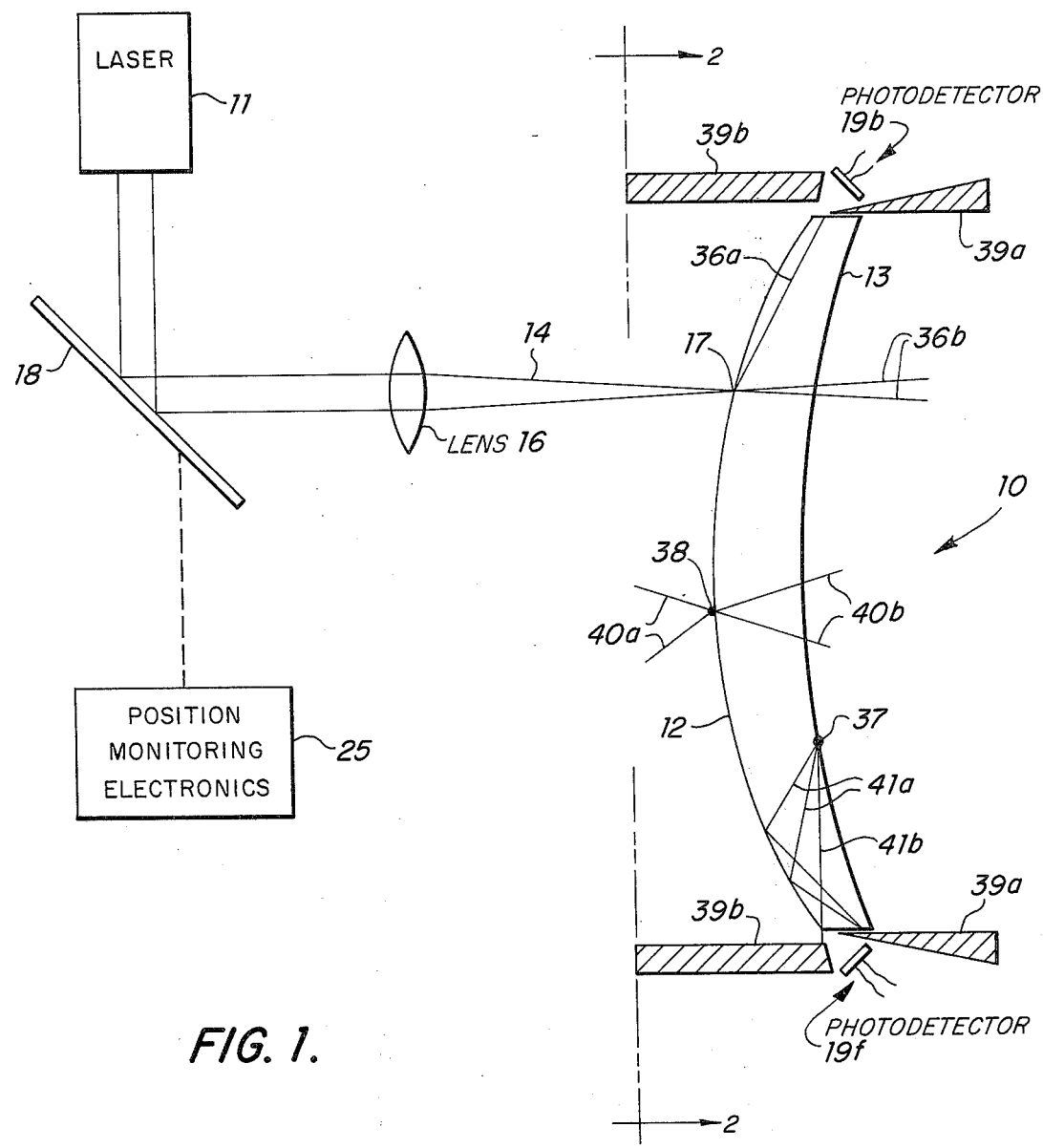
FIG. 1 illustrates, in highly schematic form, an apparatus for detecting cosmetic defects in a lens in accordance with a presently preferred embodiment of the invention.
Figure 2:
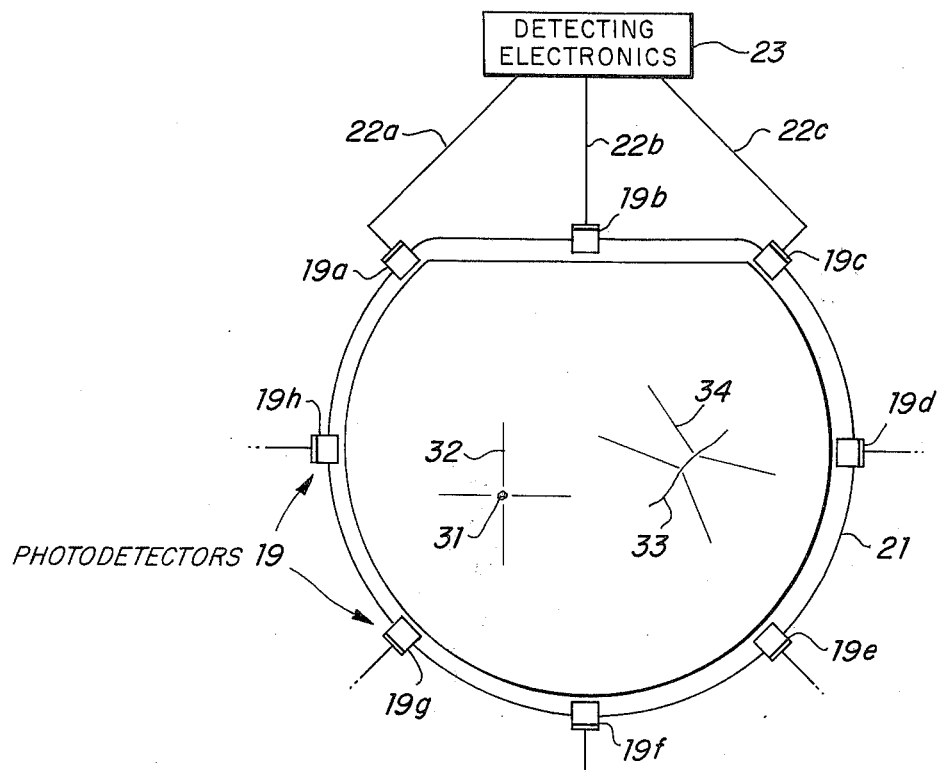
FIG. 2 illustrates the apparatus of FIG. 1 looking in the direction of arrows II—II in FIG. 1.

FIGS. 1 and 2 illustrate, in highly schematic form, the general arrangement of components for examining a surface of a lens 10 for cosmetic defects. Inasmuch as the present invention has been primarily designed for the purpose of detecting cosmetic defects on the front surface of semifinished opthalmic lenses, it is toward this application that the following description will be primarily directed, however, it should be clearly understood that the invention should not be so limited. The invention could readily be utilized to examine either surface of a lens or other transparent element designed for use in any one of a wide variety of applications.

In the manufacture of ophthalmic lenses, the lens manufacturer conventionally grinds and polishes or otherwise reduces the front convex surface 12 of a lens to a desired finished curvature, usually spherical, and leaves the rear concave surface 13 in a partially finished condition with, perhaps, no more than a roughly ground curvature thereon. This partially completed lens, which is referred to as a semifinished lens, is then sent to an optical wholesale laboratory where the rear surface is ultimately finished to satisfy the specific prescription requirements of an individual patient.

Before the manufacturer sends the semifinished lens to the laboratory, however, he must examine it to ensure that it is of acceptable quality. To be able to effectively accomplish this examination in an automatic manner, it should be apparent that the system provided must be able to discriminate between defects which are present on or under the finished front surface 12 and defects which are present on the unfinished rear surface 13 because defects on that surface will generally be removed later when the lens is finished to prescription and, thus, are of no great concern. Also, this system must be able to effectively distinguish between actual cosmetic defects such as scratches and chips and mere surface contamination such as fingerprints or dust. The present invention is capable of accomplishing this required descrimination in a manner to be described in detail hereinafter.

Basically, with reference to FIG. 1, the lens 10 under examination is positioned to be illuminated by a narrow beam of light 14 directed to it from a laser 11 or other suitable light source. Preferably, light beam 14 is brought to a substantial focus on the lens surface 12 to be examined and a focusing lens system schematically illustrated by lens 16 is provided in the beam path for this purpose. By focusing the beam onto the surface being examined in this manner, the cross-sectional area of the beam when it impinges surface 12, i.e., at point 17, can be kept quite small (e.g., from $10\mu$ to 10 mm.) and, hence, capable of distinguishing very small defects. Also, this feature permits better discrimination between front and rear surface defects as will be explained more clearly hereinafter.

The system provided preferably also includes a suitable scanning system, schematically illustrated by scanning mirror 18, to permit the beam to be scanned back and forth over the entire surface of the lens so that all portions thereof can be examined or, alternatively, to direct the beam to desired locations on the lens. Other types of structures could also be used if desired to direct one or more beams to the lens surface as recognized by those skilled in the art, and these alternative structures are meant to be included in the present invention. A scanning rate that would permit the entire lens to be examined in one second or less can effectively be employed, although, it should be obvious that the time required to scan the entire lens will depend in part on the diameter of beam 14 when it impinges upon surface 12 and, accordingly, increased speeds might require that the beam diameter be increased somewhat.

For detecting and analyzing the manner in which light beam 14 is affected as a result of impinging upon lens surface 12, an array of photodetectors, generally identified by reference number 19 are provided. As more clearly shown in FIG. 2, detector array 19 preferably comprises a plurality of individual photodetectors 19a, 19b, 19c, etc. of conventional type supported in a substantially symmetrical pattern around the edge of lens 10 and oriented to receive light passing through the edge of the lens. The number of individual detectors in the array should be at least four in number, although a larger number, for example, eight is preferred for greater accuracy. The individual detectors may conveniently be mounted in a suitable ring support 21 designed to receive the lens therein such that the detectors will be spaced as closely as possible to the edge of the lens. The lens itself may be supported by resting it on a base plate or the like for easy placement and removal. As illustrated in FIG. 1, photodetectors 19 are also positioned nearer the front face 12 of the lens 10 and light shields 39a and 39b are provided to prevent light from reaching th detectors except through a relatively narrow opening adjacent the front of the lens edge. This structure and orientation permits the system to effectively discriminate between front and rear surface defects and between actual defects and external contamination as will be explained more fully hereinafter.

The outputs of the individual detectors 19a, 19b, 19c, etc. are coupled by means of leads 22a, 22b, 22c, etc., respectively, to suitable detecting electronics 23 capable of analyzing the received signals as will be explained hereinafter.

The operation of the present invention for detecting and analyzing cosmetic defects on or beneath the surface 12 of lens 10 will now be explained in detail with reference to FIGS. 1 and 2. Initially, let it be assumed that beam 14 is impinging upon an area of lens surface 12 that is free of defects. In such a circumstance, the passage of the light beam through the lens will be uninterrupted and accordingly, will, for the most part, follow a normal path and pass directly through the lens, being altered, if at all, only by the refractive power of the lens. Accordingly, no light, or almost no light, will reach the detector array 19 and no signals will be generated therefrom.

Now, let it be assumed that lens surface 12 is impinged by light beam 14 at a location that does contain a defect (e.g., at point 17). When this happens, the defect will interfere with the passage of light beam 14 through the lens and cause at least part of it to be either scattered or deflected laterally out of its normal path through the lens (path 36b). When this happens, some of the light (e.g., ray 36a) will be seen by one or more of the detectors which, in turn, will generate signals indicating the presence of the defect. By properly monitoring the outputs of the detectors 19a, 19b, 19c, etc., the presence of the defect in the lens can readily be ascertained.

Merely identifying the presence of a defect, however, is not adequate for the purposes of the present invention, and, in fact, to accomplish only this function, one or two detectors positioned in any one of a variety of locations would be sufficient. To satisfy the requirements of the present invention, the system should also be able to provide information regarding the defect location, its size and shape, and also be able to ensure that the defect is a true cosmetic defect located on the front surface of the lens.

The present invention provides this capability through the use of symmetrical detector array 19, and by properly orienting the array relative to the lens, accurate analysis of the lens and its defects becomes possible. Let us consider, for example, the effect on the light beam 14 of a chip or pit on surface 12 as indicated by area 31 in FIG. 2 which is of a size substantially equal to or less than the cross-sectional area of the beam when it impinges upon surface 12. Such a defect will, upon being struck by light beam 14, scatter light laterally of the lens. Furthermore, it will tend to scatter light in all directions as illustrated by lines 32 with the result being that at least some light will ultimately reach all or most of the detectors 19a, 19b, 19c, etc. Accordingly, if the detector outputs are examined in sequence, a generally uniform DC output signal will be produced and this will indicate that the defect is of the chip or bubble type (a bubble will generally produce a better DC signal than a more irregularly shaped chip to permit these two types of defects to be distinguished).

The location of the chip found as described above can readily be ascertained by monitoring the position of the scanning light beam with position monitoring electronics 25 (FIG. 1) or with an optional positioning feedback system. The magnitude of the defect can be analyzed as a function of the intensity of the scattered light when the defect is smaller than the cross-sectional area of the light beam as more severe defects will tend to scatter more light. In this regard, a set of tolerance standards can readily be established within detecting electronics 23 relating defect size as a function of defect shape. Specific electronics for doing this is available in the art and does not form part of the present invention. Larger defects must be evaluated for shape by performing an appropriate scanning sequence.

Let us now consider the effect of a scratch as illustrated at 33 in FIG. 2 on the light beam 14. When the beam strikes a defect of this type, the light will not be scattered in all directions, but instead will tend to be scattered in directions perpendicular to the axis of the scratch as illustrated by lines 34. Thus, in FIG. 2, most of the light scattered by scratch 33 will be received by detectors 19a and 19e, while the remaining detectors will receive lesser amounts or no illumination depending upon their orientation relative to the scratch. Such a defect thus produces a highly asymmetrical scattering pattern and by observing the detector outputs in sequence, an AC signal will be produced to indicate not only that the defect is a scratch but also its general orientation.

The precise orientation and length of the scratch can also be more fully defined (as can the precise shape of large chips or bubbles) by developing an accurate contour shape of the boundary of the defect as beam 14 is scanned across the entire lens surface. The electronics for accomplishing this type of analysis is also well known in the art and need not be described in detail here. Suffice it to say, however, that by examining the scattering profile of the defect, the intensity of the scattered light as a function of the scattering profile of the defect, and, if necessary, the contour map of the defect, an accurate identification of the defect as to type, size and orientation can readily be determined. By correlating this information with the position of the scanning beam 14, its precise location can also be readily ascertained.

As mentioned previously, it is also necessary that the system be able to ascertain that the defect that has been analyzed as described above be on the front surface 12 of the lens rather than on the rear surface 13 and also that it be a true cosmetic defect and not a false signal produced by surface contamination such as dust or fingerprints. This necessary discrimination is effectively obtained by mounting the detectors around the edge of the lens so that they will only see light that is scattered within the body of the lens as shown in FIG. 1, and by including suitable light shields 39a, 39b, also shown in FIG. 1, which ensure that light does not come from the rear surface.

Let us first consider the effect of surface dust or fingerprints on surface 12 on impinging light beam 14. Light that is scattered by a dust particle 38 (FIG. 1) or other matter external to the glass will be mostly either reflected away from the lens (lines 40a) or refracted by the glass and pass on through the lens (lines 40b), and, thus, not reach the detectors. Although for a few dust positions some light will tend to reach the detector, this light will be very divergent and will strike the lens surface at such a high angle that only a small amount of it will be seen by the detectors and the detecting electronics 23 can easily be adjusted to ignore these weak signals.

The effect of rear surface defects can be explained with reference to FIG. 1 wherein a defect 37 is shown. Since the detectors are mounted behind appropriate light shields 39a, 39b, light scattered by rear surface defects will not be able to reach detector 19f directly as illustrated by light ray 41b. Light can reach the detectors only after multiple scattering at lens edges or from other defects, which reduces its intensity and even then only when the light is scattered at precise angles (e.g., rays 41a will still be blocked because of mask 39a). In addition, the beam 14 will be defocused when it reaches the second surface because it has been intentionally focused onto front surface 12, and, as a result, any defects on this second surface will scatter only a small percentage of the impinging light. Thus, the low intensity light from a rear surface defect that is able to reach the detectors can readily be ignored by suitable thresh holding circuitry in the electronics.

Figure 3:
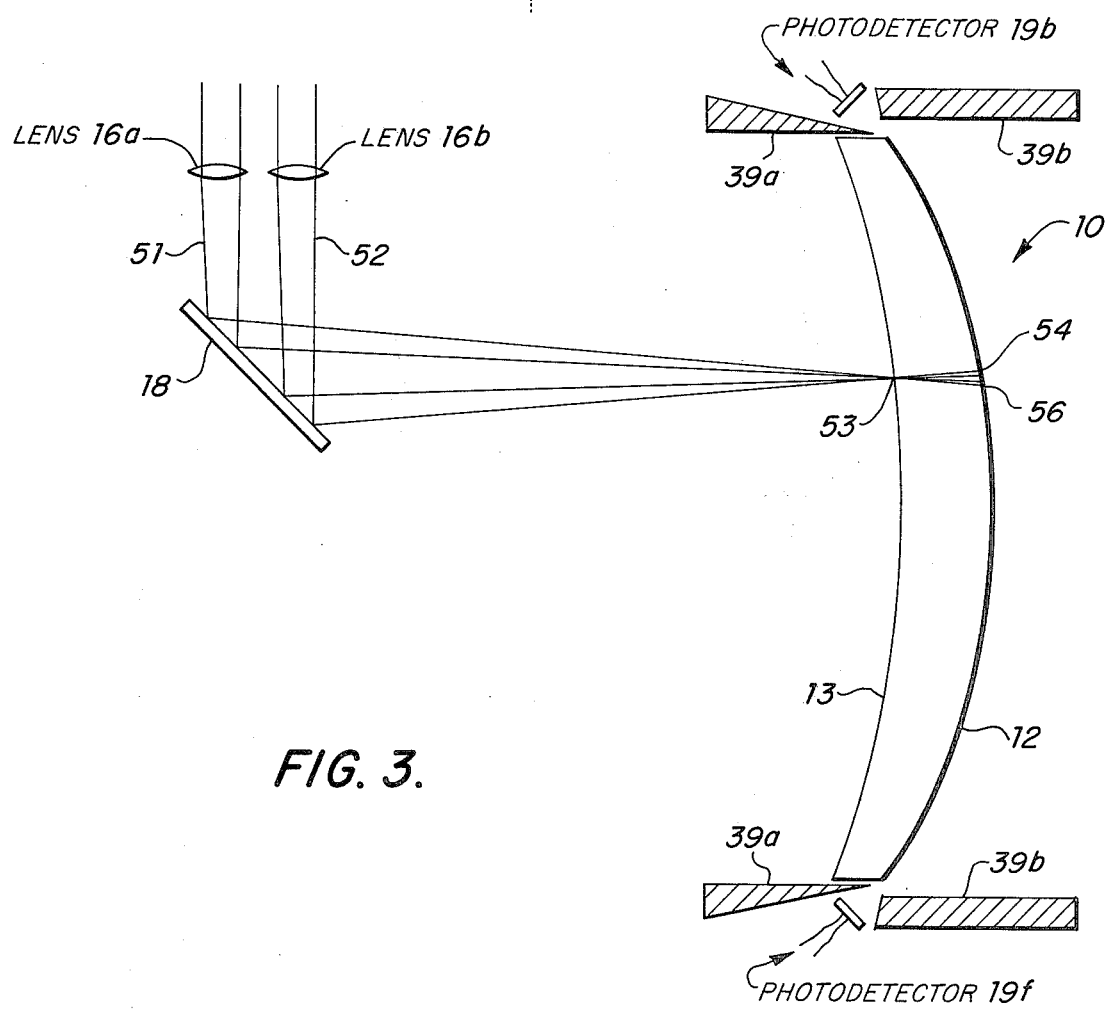
FIGS. 3 and 4 illustrate alternative embodiments of the present invention.

FIG. 3 illustrates an alternative embodiment of the invention which, for certain defect locations, can provide more precise discrimination between front and rear surface defects. This embodiment can be used in place of the embodiment of FIGS. 1 and 2, or, if desired, in conjunction with it to ensure greater accuracy.

In this embodiment, a pair of light beams 51 and 52 are utilized to illuminate the lens and instead of being brought to a focus on the front surface 12 under examination, they are brought to a focus on the rear surface 13. In this configuration, the light beams strike the rear surface first. More particularly, the two beams are directed by optical systems 16a and 16b and by scanning system 18 to lens 10 so as to be brought to a focus at the same position on the back surface 13 so that they will be superimposed upon one another at the point where they impinge on the rear surface (e.g. at point 53). Also, the two beams are differentiated from one another as by temporally modulating them at different frequencies, polarizing them at different angles, by making them of different wavelengths, or by some other technique so that detector output signals representing each beam can be separated from one another.

With this construction, when light reaches one or more of the detectors in detector array 19 as a result of being scattered by a rear surface defect, light from both beams will have struck the defect simultaneously (since they are superimposed on one another) and light from both beams will reach the detectors simultaneously. When the detector output signals representing each beam are then separated and subtracted from one another by detector electronics 23, they will exactly cancel out, indicating that the defect is on the rear surface.

If, however, the defect is on the front lens surface 12 under inspection, a different result will be obtained. Specifically, after beams 51 and 52 pass lens surface 13, they will begin to diverge from one another, with the result that they will be separated when they strike the front lens surface 12. In other words, one of the beams will strike one area 54 of surface 12 while the other beam will strike a different area 56. Any defect on the front surface, therefore, will be struck by only one of the beams at a time and light from only one of the beams will reach the detectors at a time. If the outputs of the detectors are then analyzed and rectified, a strong positive signal will result indicating that the defect is, in fact, on the front surface.

Figure 4:
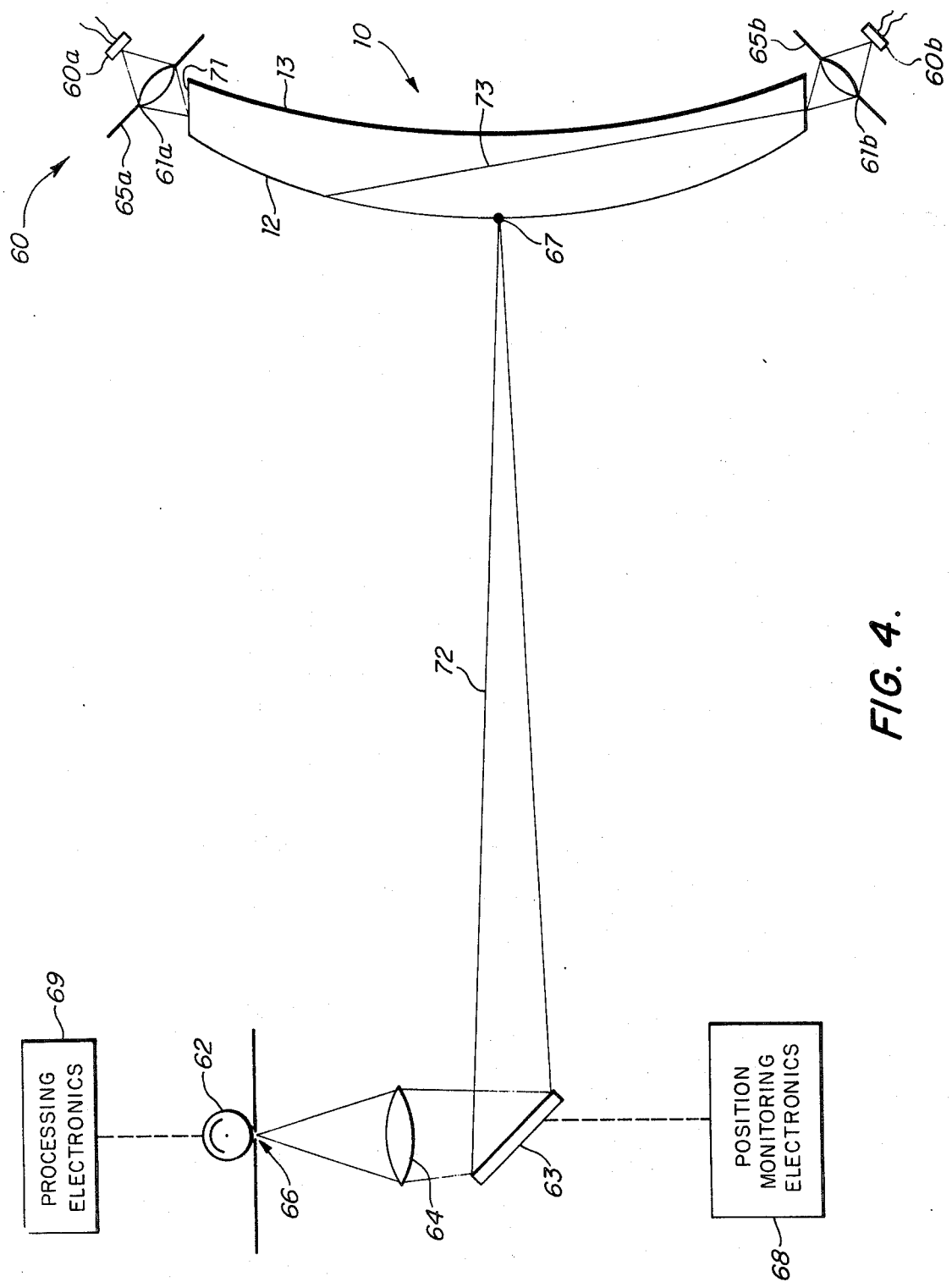

FIG. 4 illustrates a further embodiment of the invention which is generally similar to the embodiment of FIGS. 1 and 2 except that the light source and the detectors have been interchanged. Specifically, in FIG. 4, the ring of photodetectors has been replaced by a similar ring of light sources 60, while a single photodetector 62 has been positioned at the location occupied by the light source 11 of FIG. 1.

The ring of light sources 60 consists of a plurality of individual light sources 60a, 60b, etc. (only two being shown in the FIG.) such as light emitting diodes or the like, positioned to illuminate the interior of lens 10 through the edge 71 thereof. Preferably, this is accomplished by focussing the light from the diodes substantially on the edge of the lens via focusing lenses 61a, 61b, etc., such that after passing through the edge of the lens under examination, the light will diverge and illuminate a substantial portion of the lens interior. Additionally, the light sources are positioned near the front surface 12 of lens 10 and are aligned relative to it such that the light therefrom will impinge upon front surface 12 at angles less than the critical angle so that the light will be totally internally reflected therefrom. This alignment can be accomplished fairly easily with a slight amount of experimentation and is important for reasons to be explained hereinafter. As in the previous embodiments, masking means are also preferably provided to prevent unwanted light rays from entering the lens. These masks can take the form of masks 65a or 65b which permit only the light that is passed through focussing lenses 61a and 61b, respectively, to reach lens 10.

To monitor the lens 10, a suitable photodetector such as a photomultiplier tube 62 is positioned to receive light directed thereto from a scanning mirror system schematically illustrated at 63. As previously, the scanning mirror is adapted to scan across the lens surface 12 and examine each area thereof. Light received by the scanning mirror is preferably focussed by lens 64 through a pin-hole 66 onto the photodetector 62 to permit examination of precise areas of the lens 10 by photodetector 62.

The system of FIG. 4 operates in the following manner. Initially, the interior of the lens is illuminated by each of the light sources 60a, 60b, etc. preferably in a rapid sequence, although parallel illumination may also be employed, if desired. In the absence of any defect in the lens, all of the light will be totally internally reflected within the lens and eventually leave the lens through its edge. Accordingly, no light will reach the detector 62 as mirror system 63 is scanned across surface 12. When, however, a defect is present, e.g., defect 67, light will be scattered by it and a portion of this scattered light will pass through surface 12 and be picked up by mirror 63 as it is scanned across the lens. This received light (indicated by ray bundle 72) will thus be directed to detector 62 and be identified.

The precise location of the defect can be accurately determined as before through the use of suitable position monitoring electronics 68 which monitors the position of the scanning system 63. To identify the type of defect present, a technique similar to that described above can also be employed. Specifically, a scratch will exhibit a one-dimensional scattering pattern, while a bubble or chip will scatter light generally equally in all directions. Therefore, by illuminating the lens with each of the individual light sources 60a, 60b, etc. in sequence or by otherwise discriminating between the light from each of the individual sources (such as by varying their frequency, for example) the scattering profile of the particular defect can be readily ascertained. Conventional processing electronics schematically illustrated at 69 is provided for this purpose.

Because, in the absence of a defect, all the light directed to the lens will be totally internally reflected by surface 12, any external contamination on that surface such as dust or fingerprints will not scatter the light and, hence, no light will reach the detector. Also, by properly directing the light from sources 60 onto the front surface 12, light can be prevented from illuminating the back surface 13. This will prevent any defects on the back surface from scattering light onto the detector. This is illustrated in FIG. 4 by rearmost light ray 73 which does not touch surface 13.

The embodiment of FIG. 4 can be used in place of the embodiment of FIGS. 1 and 2 in most applications and provides the advantage of greater flexibility in permitting a wide variety of processing techniques to be carried out. For example, it is possible to replace the single detector 62 with a plurality of detectors arranged in an array to permit larger areas of the lens to be examined or to increase operating speed. Its principal disadvantage is that there is not as much light available to be seen by detector 62 as in the previous embodiments. The light that is available, however, is adequate for accurate results.

It is also somewhat more important in this embodiment that the edge of the lens be of relatively good quality so as to not scatter the light to any significant extent. It has been found, however, that most lens blanks do have edges of adequate quality and need not be smoothed prior to inspection. In any event, any signals produced by the edge are distinguishable from the signals produced by a defect and, thus, can be disregarded by processing electronics 69.

In a typical application of the embodiments of the invention, a lens can accurately and completely be examined in a matter of a few seconds or less. For example, if scanning system 63 scans across the lens in lines 1/10 of a millimeter wide at a scan rate of from about 100 to about 10,000 scan lines per second, a typical 58mm lens can be examined in from less than a tenth of a second to about six seconds depending on the scan rate. Corresponding to such a scan rate, the individual light sources 60 should be turned on and off at a much faster rate of from about 60kHz to about 6MHz so that, for example, 8 sources can be sequenced at such a rate that the detector can detect the effect of a defect on the light coming from each source.

Thus, in conclusion, a system has been described which is effective in automatically detecting cosmetic defects on or beneath the surface of a lens under inspection. Furthermore, the system is highly effective because it is able to distinguish between actual cosmetic defects which are present on the lens surface being examined and defects on the opposite lens surface which are not of concern and surface debris such as dust or fingerprints which can be merely wiped off. Finally, the system is able to provide information regarding defect type, size and position and thus provides a valuable tool for classifying defects and for identifying the causes of the defects to permit improvement of the lens manufacturing operation.

The system is also especially suited for detecting small round defects which occur at the edge of a bifocal segment in multifocal lenses since the scattering pattern produced by the defect will be different from that produced by the segment edge itself. The detection of defects of this type is often quite difficult by conventional inspection methods.

The system has also been designed so that it may be readily incorporated into existing production lines. In this regard, it can readily be made a part of a general purpose automated lens testing system of the type described in U.S. Patent Application Ser. No. 346,366, now U.S. Pat. No. 3,877,788, to Robert A. Sprague and John A. O'Brien filed on Mar. 30, 1973 and entitled METHOD AND APPARATUS FOR TESTING LENSES.

While what has been described above are presently most preferred embodiments of the invention, it should be apparent that a variety of additions, modifications and omissions may be made without departing from the spirit thereof. Accordingly, it should be understood that the invention should be limited only as required by the scope of the following claims.

What is claimed is:
1. Apparatus for detecting and analyzing defects on or beneath the surface of a lens comprising:
   a. means for supporting said lens in position to be examined, said lens having first and second opposed surfaces and a peripheral edge;
   b. examining means for examining said lens for defects located on or beneath said first surface thereof from a plurality of examining positions around the peripheral edge thereof, said examining means including:
      1. light source means for directing light through said lens, and,
      2. detector means positioned at a location removed from the normal path of said light passing through said lens but positioned to receive light directed thereto as a result of said light striking a defect in said lens, which defect causes at least a portion of said light to be scattered out of its normal path through said lens to impinge upon said detector means, said detector means including means for generating a plurality of output signals representative of the light impinging thereon, said plurality of signals corresponding to said plurality of examining positions from which said lens is examined, and,
   c. means for comparing said plurality of output signals for analyzing said defect as a function of the scattering profile of the light scattered thereby.

2. Apparatus as recited in claim 1 wherein said examining means comprises a plurality of detectors for examining said lens at said plurality of examining positions around said peripheral edge thereof, each of said detectors including means for generating output signals representative of the light impinging thereon as a result of said light striking a defect in said lens.

3. Apparatus as recited in claim 2 in which said apparatus further includes means for supporting said plurality of detectors adjacent said peripheral edge of said lens.

4. Apparatus as recited in claim 3 wherein said light source means comprises:
   a. first and second narrow beams of light, said first and second beams of light having a property difference enabling them to be distinguished from one another,
   b. means for directing said first and second narrow beams of light through said lens, said directing means including optical means for bringing said first and second beams to a focus substantially on said second surface of said lens at substantially the same position thereon such that said first and second beams will be separated from one another when they impinge upon the first surface of said lens, whereby defects on or beneath said second surface will scatter light simultaneously from each of said first and second beams and defects on or beneath said first surface will scatter light at different times from each of said first and second beams; and,
   c. wherein said comparing means includes means for discriminating between light from said first and second beams for distinguishing between defects on or beneath said second surface and defects on or beneath said first surface.

5. Apparatus as recited in claim 3 wherein said detector supporting means includes means for supporting said plurality of detectors in a substantially symmetrical pattern around the peripheral edge of said lens.

6. Apparatus as recited in claim 5 wherein said detector supporting means includes means for supporting said plurality of detectors nearer to said first surface than said second surface for enabling light scattered off of defects on or beneath said first surface to reach said detectors more directly than light scattered off of defects on or beneath said second surface.

7. Apparatus as recited in claim 6 and further including masking means for substantially permitting only light deflected off of defects on or beneath said first surface to reach said detectors.

8. Apparatus as recited in claim 3 wherein said light source means includes means for scanning a narrow beam of light across said first surface of said lens for detecting cosmetic defects on or beneath a substantial area of said first surface.

9. Apparatus as recited in claim 8 including means coupled to said scanning means for monitoring the position of any defect on or beneath said first surface as said beam of light is scanned thereover.

10. Apparatus as recited in claim 8 wherein the scattering pattern of light scattered by a defect is a function of the type of defect and wherein said comparing means includes means for detecting the scattering pattern of said deflected light for providing information regarding the type of any defect on or beneath said first surface.

11. Apparatus as recited in claim 10 wherein said scattering pattern detecting means includes means for examining the output signals from said plurality of detectors in sequence.

12. Apparatus as recited in claim 8 wherein said light beam directing means further includes optical means for bringing said narrow beam of light to a focus substantially adjacent said first surface of said lens such that the cross-sectional area of said beam will be only a fraction of the total area of said first surface when said beam impinges upon said first surface.

13. Apparatus as recited in claim 12 wherein said optical means includes means for causing said beam of light to be out of focus when it impinges upon said second surface of said lens such that light scattered off of defects on or beneath the first surface of said lens will be of a somewhat higher intensity than light scattered off of defects on or beneath the second surface of said lens, and wherein said comparing means includes threshholding means for distinguishing between output signals above and below a specified level whereby defects on or beneath the first surface can be distinguished from defects on or beneath said second surface.

14. Apparatus as recited in claim 1 wherein said examining means comprises a plurality of light sources supported around said peripheral edge for directing light through said lens from said plurality of examining positions and wherein said detector means includes means for generating a plurality of signals representative of light striking said defect from each of said plurality of light sources.

15. Apparatus as recited in claim 14 wherein said apparatus further includes means for supporting said plurality of light sources around said peripheral edge for directing light into said lens through said edge.

16. Apparatus as recited in claim 15 wherein said light source support means includes means for supporting said plurality of light sources in a substantially symmetrical array around the edge of said lens.

17. Apparatus as recited in claim 15 wherein said detector means includes means for scanning across said first surface for detecting the light scattered off of a defect.

18. Apparatus as recited in claim 17 including means for actuating said plurality of light sources in sequence for striking any defects with light from each of said light sources in sequence.

19. A method for detecting and analyzing cosmetic defects on or beneath the surface of a lens comprising:
 a. directing a narrow beam of light through said lens;
 b. positioning a plurality of photodetectors around the edge of said lens for receiving light directed thereto as a result of said beam of light impinging upon and being scattered by a defect on or beneath said surface of said lens;
 c. monitoring the output signals from each of said plurality of photodetectors; and,
 d. comparing said monitored output signals with one another for analyzing said defect as a function of the light scattered thereby.

20. A method as recited in claim 19 wherein the scattering pattern of light deflected by a defect is a function of the type of defect and wherein said comparing step includes the step of determining the scattering pattern of said scattered light for identifying the type of defect present on or beneath said surface of said lens.

21. A method as recited in claim 20 wherein said positioning step comprises positioning said plurality of detectors in a symmetrical pattern around the edge of said lens.

22. A method as recited in claim 20 wherein said light beam directing step includes the step of scanning said light beam over said surface of said lens for detecting any defects on or beneath a substantial area of said lens surface.

23. A method as recited in claim 22 and further including the step of bringing said light beam to a substantial focus on said surface of said lens.

24. A method for detecting and analyzing cosmetic defects on or beneath the surface of a lens comprising:
 a. directing light into said lens from a plurality of illuminating positions around the peripheral edge of said lens;
 b. detecting light scattered by any defect on or beneath said lens surface from each of said illuminating positions and generating a plurality of signals representative of the light scattered by said defect from each of said plurality of illuminating positions; and,
 c. comparing said plurality of signals for analyzing said defect as a function of the light scattered thereby.

25. A method as recited in claim 24 wherein said directing step further comprises directing light into said lens from said plurality of positions in sequence.

* * * * *